United States Patent [19]

Wulf et al.

[11] 3,940,431

[45] Feb. 24, 1976

[54] DIMETHYL TEREPHTHALATE PREPARED BY THE ESTERIFICATION OF TEREPHTHALIC ACID

[75] Inventors: Horst-Dieter Wulf; Ferdinand List; Kurt Wember; Norbert Wilke, all of Marl, Germany

[73] Assignee: Chemische Werke Huls Aktiengesellschaft, Marl, Germany

[22] Filed: May 18, 1973

[21] Appl. No.: 361,597

[30] Foreign Application Priority Data

May 20, 1972 Germany............................ 2224869

[52] U.S. Cl.............. 260/475 R; 23/279; 23/288 K; 23/288 E
[51] Int. Cl.² ........................................ C07C 69/82
[58] Field of Search ................................ 260/475 R

[56] References Cited
UNITED STATES PATENTS

| | | |
|---|---|---|
| 3,227,743 | 1/1966 | Shaw et al. ........................ 260/475 |
| 3,364,251 | 1/1968 | Benning et al. ..................... 260/475 |
| 3,377,376 | 4/1968 | Gainer et al. ....................... 260/475 |
| 3,617,226 | 11/1971 | List et al. ............................. 260/475 |
| 3,676,485 | 7/1972 | Lewis et al. ......................... 260/475 |

FOREIGN PATENTS OR APPLICATIONS

| | | | |
|---|---|---|---|
| 1,110,684 | 4/1968 | United Kingdom................. | 260/475 |
| 1,933,946 | 1/1971 | Germany ............................ | 260/475 |
| 1,212,063 | 3/1966 | Germany ............................ | 260/475 |

Primary Examiner—Lorraine A. Weinberger
Assistant Examiner—Jane S. Myers
Attorney, Agent, or Firm—Gilbert L. Wells

[57] ABSTRACT

Dimethyl terephthalate is prepared by the continuous esterification of terephthalic acid in the gas phase by evaporating solid terephthalic acid in a pre-reactor by means of a hot methanol vapor stream, conducting the gas mixture through a solid bed catalyst in a follow-up reactor, and recirculating a portion of the reaction product to the pre-reactor.

9 Claims, 4 Drawing Figures

DIMETHYL TEREPHTHALATE PREPARED BY THE ESTERIFICATION OF TEREPHTHALIC ACID

BACKGROUND OF THE INVENTION

The field of the invention is esters and processes of making the same from polycarboxylic acids. The present application is particularly concerned with the preparation of dimethyl terephthalate by the esterification of terephthalic acid.

The state of the art of preparing dimethyl terephthalate may be ascertained by reference to the Kirk-Othmer "Encyclopedia of Chemical Technology", 2nd Ed., Vol. 15 (1968), pages 466–467 under the section "Current Commercial processes for Polymer-Grade Dimethyl Terephthalate", and by reference to U.S. Pat. Nos. 2,876,252 of Rudolf Lotz et al., which issued Mar. 3, 1959 and 3,617,226 of Ferdinand List et al., which issued Nov. 2, 1971, and German Pat. Nos. 1,088,474 (corresponding to British Pat. No. 933,960), of Walter Schimming, published Sept. 8, 1960; 1,188,580 and 1,933,946 of Ferdinand List and Helmut Alfs, published Jan. 21, 1971, the disclosures of which are incorporated herein.

The state of the art of fluidized beds, particularly for use in catalysis and gas-solid reactions, may be ascertained by reference to Kirk-Othmer ibid, Vol. 9 (1966), under the section "Fluidization", pages 398–445.

It is well known that terephthalic acid is a raw material for the production of polyester fibers. Because ordinary commercial terephthalic acid is not pure enough for the polycondensation reaction, the terephthalic acid must be first purified. Because of the unsuitable physical properties of the commercial terephthalic acid, the purified product is very costly. In most cases one uses the dimethylester of terephthalic acid for the purification of the same and this is recovered by alcoholysis with methanol and precondensation with glycol or other diols.

Because of these difficulties, there is substantial interest in a more economical method for the esterification of terephthalic acid. Methanol, because of its low price and molecular weight, is the most suitable alcohol in spite of the chemical and physical difficulties connected with the esterification with methanol. Since terephthalic acid is practically insoluble in boiling methanol, esterification at an adequate rate can only take place in a pressure tight apparatus made of high alloyed steel.

One method has been developed in which terephthalic acid is partially esterified in the gas phase with superheated methanol vapor in the presence of an inert gas as a carrier. This method, as disclosed by U.S. Pat. No. 2,876,252 reacts powdered terephthalic acid with methanol at about 300°C with the addition of a catalytic amount of an acid and it is blown into a reaction pipe. This method results in a relatively low yield with a low purity. According to German Pat. No. (DB-PS) 1,088,474, powdered terephthalic acid is reacted with methanol, and if necessary in the presence of nitrogen, by introduction into the fluidized bed of a catalyst. The mixture is reacted at a high temperature of about 300°C to instantly form a dimethylester which is removed with the excess methanol and reaction water. The dynamic properties of a fluidized bed in general are not particularly advantageous to the reaction since the particle size distribution of the terephthalic acid, the fluidizing of the acid and the catalysts can form undesirable channels in the bed. They must, therefore, be carefully adjusted with respect to one another so that one or both of the components are not carried out of the reactor.

German Pat. No. (DB-PS) 1,188,580 teaches the esterification of terephthalic acid by vaporization in a superheated methanol vapor stream impinging upon a fixed catalyst. The terephthalic acid in pellet form is heated to 315° to 345°C, together with methanol, in a sublimation zone at about 400°C and they are vaporized and esterified in a follow-up reactor at about 300°C. The heat necessary in the sublimation reactor for vaporizing the terephthalic acid can be provided by the heat content of the superheated methanol. This simple esterification method permits heating the terephthalic acid from about 20°C to a medium sublimation temperature of 330°C. Complete evaporation at this temperature requires 10 times by weight of methanol heated to 400°C to provide for a continuously operating sublimator.

Compared with this, U.S. Pat. No. 3,617,226 discloses a method and apparatus in which powdered terephthalic acid is in solid contact with a horizontally lying cylindrical container, and reacts with a flowing stream of methanol vapor at a temperature of between 300° and 320°C while being mechanically stirred. The particle size of the catalyst and acid need not be the same and the terephthalic acid dimethylester produced leaves the reactor in the gaseous state. Because the esterification speed at this temperature is extraordinarily high, the reaction of the terephthalic acid and the space/time yield are dependent upon technical factors such as diffusion speed, ratio of the catalyst active surface area to terephthalic acid, material transport and heat exchange and dwell time. With respect to a given unit of time for carrying out the reaction, the dwell time and esterification conversion is directly dependent upon the available catalyst surface and the amount of available heat required for the vaporization of terephthalic acid or dimethyl terephthalate. In this case, the catalyst surface area available per unit of time with respect to the useable volume of the cylindrical container is ascertained, while the transferable amount of heat is limited by this surface area, except for the possible temperature difference between the heating medium and the reaction components. An increase in size of such a cylindrical reactor results in a smaller ratio of surface to volume so that a greater esterification capacity is limited by the technical problems associated with the construction of a large cylindrical reactor with the greatest possible surface area and the necessary stirring mechanism.

SUMMARY OF THE INVENTION

Having in mind the limitations of the prior art, it is an object of the present invention to resolve the limiting factor of surface to volume. In general, however, it is an object of the invention to improve the functional capacity of an esterification method in which terephthalic acid is partially or completely vaporized in a methanol stream and esterified directly after on a solid bed catalyst.

A further object of the invention is to achieve the highest possible conversion of terephthalic acid with a minimum amount of excess methanol. It is self-evident that maximum utilization of a given apparatus for the simplified preparation of a reaction mixture must have as its goal the complete esterification of the terephthalic acid.

The esterification of terephthalic acid is carried out in two steps:

I. 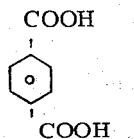 $+ CH_3OH$ 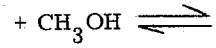 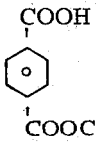 $+ H_2O$

II. 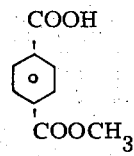 $+ CH_3OH$ 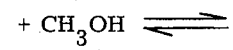 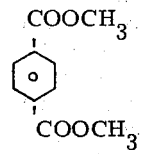 $+ H_2O$

The terephthalic acid monoester (boiling point 303°C at 760 mm Hg) formed by I completely evaporated at the reaction temperature and it is unavoidable that at high production levels the monoester is carried out in the circulating gas stream. Because of this, it is better to recirculate the gas stream monoester indirectly back through a second reactor in which the same catalyst is placed as a solid mass as it is in the main reactor. This is done rather than recirculating the gases back through the main reactor in order to complete the esterification of the excess methanol. An apparatus of this type is disclosed in German Pat. No. (DT-OS) 1,933,946 whereby the entire esterification takes place in a solid bed while the fluidized bed oven is utilized for maintaining the dispersion and partial vaporization of the solid terephthalic acid in methanol vapor.

According to the present invention, dimethyl terephthalate DMT is prepared by the continuous esterification of terephthalic TA with methanol in the gas phase by vaporization of solid terephthalic acid by means of a hot methanol vapor stream in a pre-reactor and the introduction of this mixture through a solid bed catalyst into a follow-up reactor. The method is an improvement over the prior art comprising recirculating a portion of the hot gaseous esterification mixture from the output of the follow-up reactor back to the pre-reactor.

BRIEF DESCRIPTION OF THE DRAWINGS

The invention may best be described by reference to the drawings, wherein:

In FIG. 1, TA is introduced to pre-reactor 3 at 1 while methanol is introduced at 2. The products of pre-reactor 3 are fed to follow-up reactor 4 and the further reacted products of 4 exit at 5.

In FIG. 2, TA is again introduced to pre-reactor 3 at 1. Methanol vapor is introduced from conduit 7 through vapor jet 8 and heat exchanger 9 to pre-reactor 3 at 2. A portion of the reaction product of follow-up reactor 4 passes through recirculating conduit 6 and joins the methanol at the vapor jet 8. The improved product exits at 5.

DESCRIPTION OF THE PREFERRED EMBODIMENTS

Figure 3:
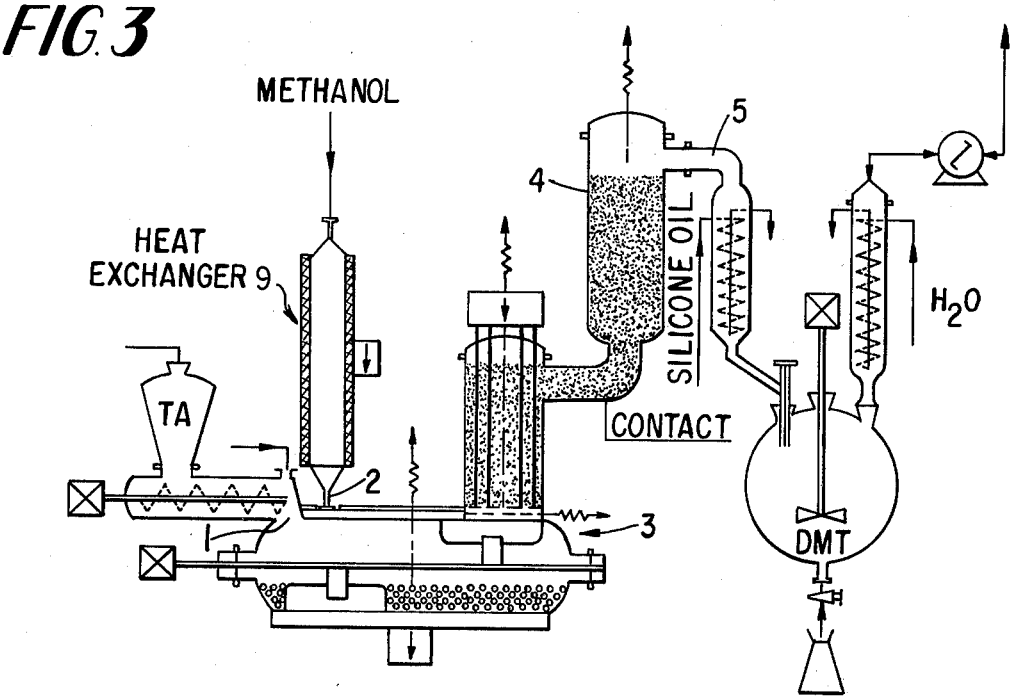
FIG. 3 is a diagrammatic representation of the apparatus of German Pat. No. (DT-OS) 1,933,946 for the continuous esterification of terephthalic acid using a fluidized bed.
Figure 4:
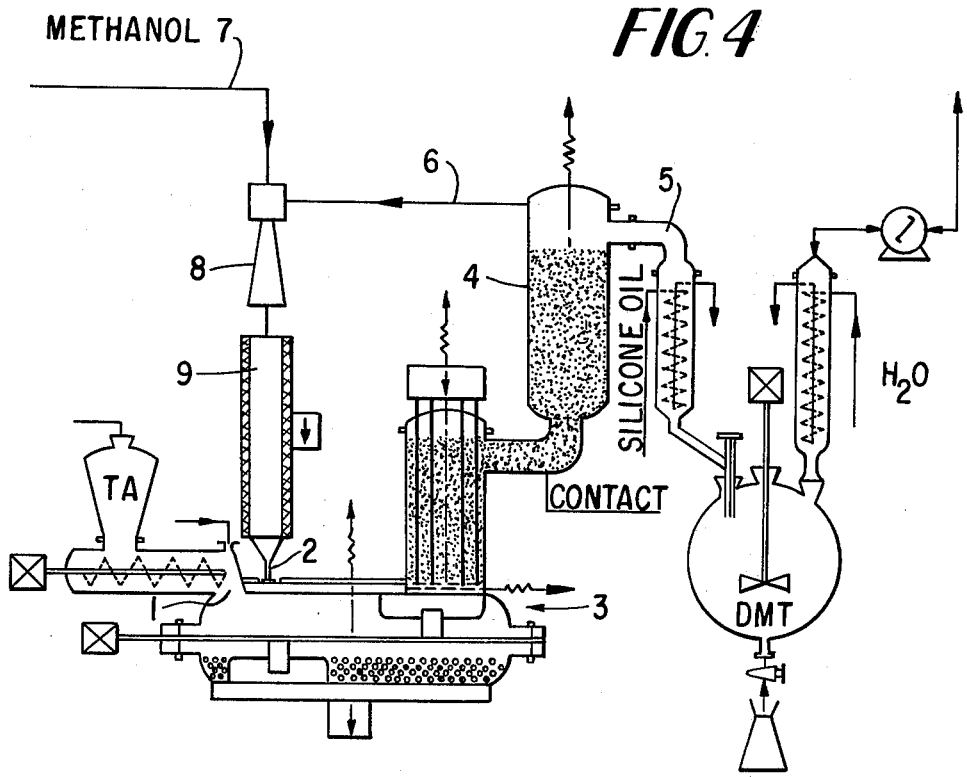
FIG. 4 is a diagrammatic representation of an embodiment of the present invention showing an improvement in the apparatus of FIG. 3.

The operation of an apparatus as illustrated in FIG. 3 consists of a fluidizing bed reactor 3 and a follow-up reactor 4 in which methanol enters at 2, and an increasing amount of terephthalic acid is introduced at 1. A portion of the terephthalic acid which has a particle size down to 5 microns is unavoidably entrained and introduced into the follow-up reactor 4. This can lead to an increase in the pressure difference between the input and output (2 and 5) and in extreme cases can lead to obstruction of the apparatus. In addition to the problem of clogging by solid particles, the reaction mixture in the main reactor at the operating temperature can become saturated with terephthalic acid vapor and a portion of this vapor can condense upon slight cooling, especially in the entrance to the follow-up reactor.

One can minimize these problems by using an adequate amount of superheated methanol in order to completely vaporize the terephthalic acid. It is apparent, however, that increasing the amount of methanol can adversely influence the economy of the method. In addition, excessive heating of the methanol requires an extra amount of heat. Furthermore, excess heating of the methanol above 330°C causes decomposition of the methanol on the catalytic surface to dimethyl ether, formaldehyde and methane. In addition, other technical problems arise in conjunction with the use of high temperatures associated with the use of high pressure steam or heat carriers.

A further object of the invention is to avoid the above-mentioned difficulties in a sure and simple manner.

These difficulties are avoided according to the invention by recirculating a portion of the output stream 5 comprising hot gaseous esterification products back into the pre-reactor 3.

The hot gaseous esterification mixture comprises dimethyl terephthalate, methanol, reaction water and traces of monomethyl terephthalate. The branched-off recirculated portion of the hot esterification gases are not brought into contact with fresh methanol vapor and nonesterified terephthalic acid until they reach full partial vapor pressure. One chooses an amount of gas to be recirculated, which is free of terephthalic acid vapor pressure, which will permit all of the non-esterified terephthalic acid in the pre-reactor 3 to pass over into the vapor phase.

Because the reaction gas after complete esterification of terephthalic acid forms two moles of water for each mole of ester, which water also is recirculated back to the pre-reactor, it was expected that the esterification equilibrium, at least to some extent, would be urged in the direction of the free acid and it was further expected that the extent of the methanol excess according to the invention should be minimized. In addition, a reduction of the speed of esterification was expected. Unexpectedly a conversion in practice of terephthalic acid of more than 99 percent was achieved, which can be increased by additional follow-up reactors in the main reaction stream.

The terephthalic acid used in the invention should be in small particles, in tablet form, or in powdered form. Preferably, powdered terephthalic acid is employed in a horizontally positioned rotatable oven similar to that disclosed in German Pat. No. (DT-OS) 1,933,946. There is substantially no esterification of the vapor mixture before entry into the solid bed. The gas mixture contains fresh and recirculated methanol, recirculated dimethyl terephthalate and recirculated reaction water in addition to fresh unreacted terephthalic acid. One can also use the particle esterification catalyst in a horizontal rotating oven of the type disclosed in U.S. Pat. No. 3,617,226. The degree of esterification depends upon the rate of flow through the apparatus and is usually between 30 and 90 percent by weight.

The method is also useful to improve the economy of the methods disclosed in German Pat. Nos. (DT-PS) 1,188,580 and 1,088,474, and other processes in which hot methanol vapor entrains terephthalic acid which is directed on to a catalyst.

By "vaporization" is meant complete transfer of all of the solid terephthalic acid into the vapor phase in order that transfer of entrained finely divided terephthalic acid with the reaction product is avoided since this is an object of the invention.

The recirculated reaction gas containing methanol vapor should be heated to about 250° to 350°C, preferably between 310° and 330°C. One chooses a temperature in agreement with the recirculating amount of reaction gas given in Table II in order that the total amount of nonesterified terephthalic acid can be vaporized without reaching the temperature in which the above-mentioned decomposition of methanol takes place.

The ratio of the recirculated gas stream is advantageously from 0.5 to 5 times that which leaves the follow-up reactor 4. A more preferable range within this range is from one to two times the output 5 of reactor 4. The values given in Table II are used to choose a suitable coordinated temperature with respect to volume of gas to be recirculated.

The gas to be recirculated is heated to about 310° to 330°C which can easily be done since it does not contain any solid matter.

Various solid matter esterification catalysts, such as the series of silicates, oxides, hydroxides or phosphates, especially silica gel as disclosed in U.S. Pat. No. 3,617,226 or German Pat. No. (DT-OS) 1,933,946, are operable in the process.

Figure 2:
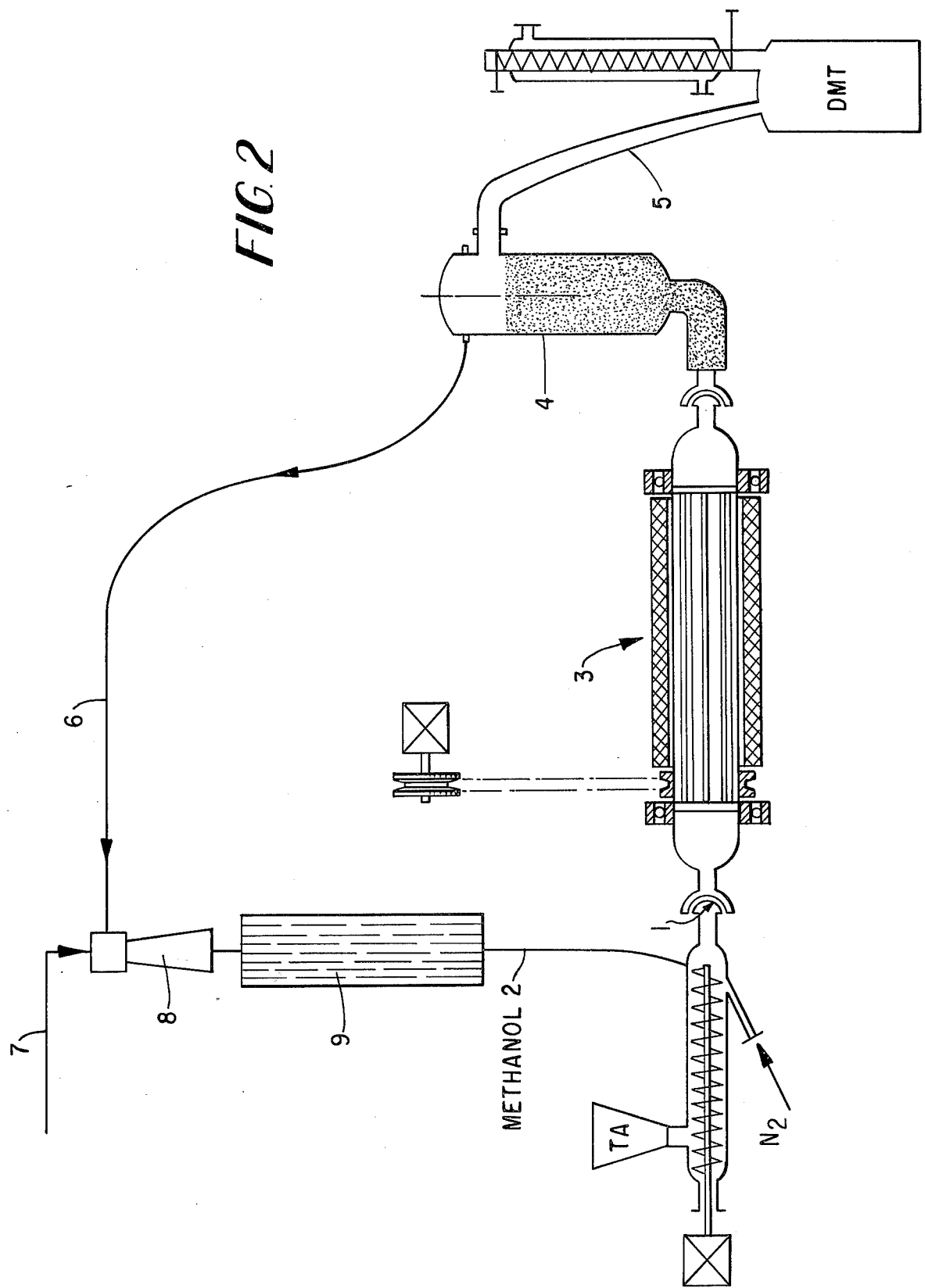
FIG. 2 is a diagrammatic representation of an embodiment of the present invention showing an improvement in the apparatus of FIG. 1 for the continuous esterification of terephthalic acid.

A schematic view of the apparatus used in the present invention is shown in FIG. 2. One can use a rotary gas blower, a compressor, or a gas jet in order to overcome the pressure drop between the input and output of the reactors whereby fresh methanol vapor is used as the propellant gas. Under these conditions, it is possible, using a minimum methanol excess and holding a maximum temperature of about 330°C, to quantitatively esterify terephthalic acid with a high space/time yield. It was unexpectedly discovered that the reduction of the dwell time due to an increase in gas volume moving through the apparatus per unit of time did not reduce the space/time yield in spite of the fact that the terephthalic acid conversion in the pre-reactor 3 is naturally less. The total catalytic surface of the solid bed catalyst 4 is fully used because the recirculated gas stream is not inhibited by the condensation of terephthalic acid which condensation leads to the formation of canals and turbulence since it no longer partially obstructs or stops the catalyst fill. This advantage of the invention permits an increase in the reaction running time as much as three times which is evident from the comparative Examples 1 and 3, which follow.

The invention is further illustrated as follows:

Table 1 discloses that the vapor pressure of terephthalic acid is 20.0 Torr (mmHg) at 320°C.

TABLE 1

| Vapor Pressure of Terephthalic Acid | |
|---|---|
| 290°C | 4.5 Torr |
| 300°C | 7.5 " |
| 310°C | 13.0 " |
| 315°C | 16.7 " |
| 320°C | 20.0 " |
| 325°C | 27.0 " |
| 330°C | 32.0 " |

At a total pressure of 1,100 Torr, which is limited in the pre-reactor 3 by the flow resistance of the follow-up reactor 4, 1.85 mole percent terephthalic acid vapor at a maximum inside temperature of 320°C is introduced into the gas stream. The amount of methanol vapor must be at least 98.15 mole percent which corresponds to 10.9 tons per hour methanol to each ton of terephthalic acid per hour. In order to maintain a water-methanol mash of terephthalic acid dimethylester, such as that obtained by cooling the reaction gas of the esterification apparatus in a transportable state, it should have a total solid content between about 25 and 30 percent, that is the terephthalic acid-methanol ratio should not be less than 1 to 3 parts by weight. In practice, the maximum vaporizable amount of terephthalic acid to be converted to dimethyl terephthalate and monomethyl terephthalate depends upon the saturation point of the vapors of terephthalic acid and the thermal transfer speed with respect to a unit of time. Since all of the limiting quality functions are variables, it is practically impossible to ascertain the exact maximum amount of vaporizable terephthalic acid. Table II gives the values for the case in which a methanol-terephthalic acid ratio of 3.0 and a saturation degree of 100 percent of the terephthalic acid is to be converted in the prereactor 3 and converted in said reactor to the extent of 30 mole percent during the formation of 10 mole percent of monomethyl terephthalate. These are minimum values. The conversion values found in practice are substantially higher, yet it permits a clear showing of the influence of recirculation in spite of the unfavorable value.

TABLE II

Maximum vaporizable amount of terephthalic acid-methanol ratio of 1 to 3 with a 30 percent conversion of terephthalic acid in reactor 3. (R is the ratio of the recirculated reintroduced mole mass; Kg/ton is the Kilogram per metric ton of added vaporizable amount of terephthalic acid)

| Temp. °C | Maximum amount of vaporizable terephthalic acid at: | | | |
|---|---|---|---|---|
| | R = 0 kg/ton | R = 1 kg/ton | R = 2 kg/ton | R = 3 kg/ton |
| 300 | 115 | 256 | 380 | 511 |
| 310 | 187 | 418 | 621 | 835 |
| 315 | 243 | 535 | 794 | 1,065 |
| 320 | 306 | 680 | 1,010 | 1,358 |
| 325 | 389 | 867 | 1,287 | 1,728 |
| 330 | 499 | 1,112 | 1,649 | 2,210 |

It can be seen from Table Ii that at a temperature of between 320 and 325°C with a recirculation of 1 the total amount of terephthalic acid is vaporized and can be conducted free from solid material with the gas stream into follow-up reactor 4. FIG. 2 shows an apparatus according to the invention that can handle a continuous flow of a methanol-terephthalic acid ratio of 3 to 1 at a suitable temperature within the given range of 290° to 330°C with recirculation of the total non-reacted terephthalic acid to vaporize and esterify the same on a solid bed catalyst.

The following examples utilize an apparatus having a solid catalytic bed according to U.S. Pat. No. 3,617,226 in a manner according to the present invention in which operation the use of recirculation is compared to reaction without recirculation. A catalytic covered rotary oven serves as the pre-reactor. The introduction of one ton of terephthalic acid per hour is normal in large scale production. These proportions do not define limits as is evident by the following examples.

EXAMPLE 1

(Comparative Example)

Figure 1:
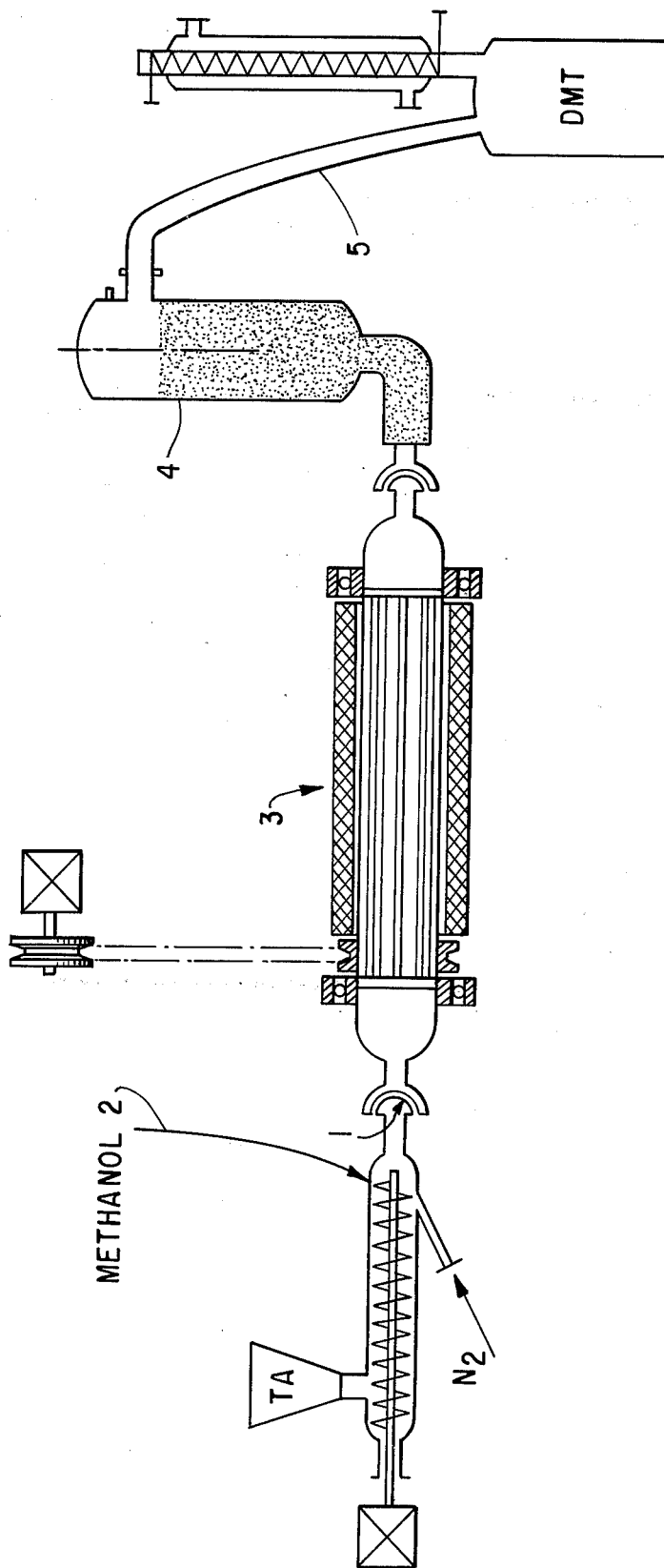
FIG. 1 is a diagrammatic representation of the apparatus of U.S. Pat. No. 3,617,226 with the addition of a follow-up reactor for the continuous esterification of terephthalic acid.

An externally steam heated pilot apparatus heated to 340° to 350°C according to FIG. 1, is provided with particulate or powdered silica gel solid bed catalyst to the extent of 30 percent of the volume of pre-reactor 3 and 90 percent of the volume of silica catalyst bed 4. Each hour, 43 kg of terephthalic acid is introduced at 1 and 129 kg methanol vapor at 340°–345°C is introduced through conduit 2. Temperatures of between 298°–300°C in the evaporator 3 and between 308°–310°C in the solid catalyst bed are noted after reaching a constant equilibrium. The pressure drop in the follow-up reactor 4 (difference between input and output) is about 110 mm of water pressure and the current necessary to operate the motors for the stirring mechanism in pre-reactor 3 is about 2.0 to 2.2 amps.

The vapor-form reaction mixture comprising dimethyl terephthalate, excess methanol, and reaction water is conducted out through conduit 5. The acid number (mg KOH per gram of substance) in the condensed separated solid portion of the reaction material 5 after 10 hours reaction time was about 2. The reaction mixture 5 also contains 0.6 percent terephthalic monomethylester in dimethyl terephthalate with an esterification ratio of 99.4 percent.

During 80 hours of the reaction, the acid number, the current and the pressure drop steadily increased to a value from 12–15, 5 amps. and 780 mm water pressure, respectively, which values are used to automatically terminate the reaction in order to prevent both, obstructing the apparatus and cessation of the operation of the same.

After cooling and opening the reactor 3, one finds the catalyst with half of its volume mixed with terephthalic acid. The follow-up reactor 4 has condensed crystalline terephthalic acid encrusted around and narrowing the opening.

EXAMPLE 2

A recirculating conduit 6 and a vapor jet 8 of FIG. 2 are added to the apparatus of Example 1. Methanol vapor from conduit 7 is forced through the vapor jet 8. Fifty kg terephthalic acid and 150 kg methanol vapor are introduced through conduit 7 per hour in the filled and heated apparatus employed in Example 1. Each hour 138 kg of hot reaction gas is recirculated with fresh methanol through the conduit 7 and vapor jet 8 back into the pre-reactor 3 which corresponds to a recirculation ratio of 0.63.

After 10 hours, the acid number of the reaction product from 5 was 1.5, the current flow in the stirring motor was 2.2 amps. and the pressure drop was 220 mm water pressure. These values remained the same for 190 hours. The variation of the acid number was between 1.0 to 2.5. After opening the apparatus, no free terephthalic acid was found in the prereactor and the entrance to the solid bed catalyst 4.

EXAMPLE 3

(Comparative example of the load comparison with 1.0 ton of terephthalic per hour)

In a production apparatus, comparable to that of FIG. 1, 1.0 ton of terephthalic acid and 3.0 tons of methanol at 340° to 345°C were introduced per hour. The temperature in the pre-reactor was between 320° and 325°C, and 330°C in the follow-up reactor. The pressure drop in the solid bed catalyst was between 1,200 and 1,500 mm water pressure. The acid number of the reaction product from the solid bed catalyst was 1.0 in the first three days of running the apparatus. Right after the beginning of the steady charge level of the apparatus, the acid number of the reaction product and the pressure drop began to increase. After 60 to 65 days of running the apparatus, acid numbers of 12 to 15 and a pressure drop of 4,500 to 5,000 mm water pressure caused further operation of the apparatus to be terminated.

Condensed terephthalic acid was found in the pre-reactor as well as in the entrance to the solid bed catalyst upon opening the apparatus.

EXAMPLE 4

In an apparatus of the same size as that of Example 3, provided with a recirculating conduit 6 according to FIG. 2, a vapor jet 8 and a heat exchanger 9 was charged in comparison to the manner of Example 3 with 30 percent hourly addition of terephthalic acid and methanol, comparatively 3.9 tons of methanol vapor to 1.3 tons of terephthalic acid per hour. By recirculating one-half of the reaction product behind the solid bed catalyst, a recirculation ratio of 1 is maintained. The temperature of heat exchanger 9, which heats the mixture of circulating gas as well as the fresh methanol, is between 338° and 342°C. The inside temperature of the vaporizer 3 is 320° to 325°C and the temperature in the solid bed catalyst is 330°C. The pressure drop of the solid bed catalyst is about 2,100 to 2,200 mm water pressure and the acid number of the dimethyl terephthalate reached a value of 0.5 to 2.5.

With everything uniform compared with the comparative example, a 30 percent increase in the space/time yield was obtained after 6 months run with the same results. A control showed no increase or buildup of terephthalic acid in the pre-reactor 3 or in the solid bed catalyst 4.

We claim:

1. In the continuous method for the preparation of dimethyl terephthalate by the esterification of terephthalic acid with methanol in the gas phase, comprising vaporizing solid terephthalic acid with a hot methanol vapor stream in a pre-reactor and introducing the reaction product of the pre-reactor into a follow-up reactor having a solid bed catalyst to produce a hot gaseous dimethyl terephthalate product stream, part of this stream being the output of the process the improvement comprising recirculating a portion of said dimethyl terephthalate product stream to said pre-reactor.

2. The method of claim 1, wherein said pre-reactor is a horizontal rotary oven.

3. The method of claim 1, wherein said solid terephthalic acid is vaporized in the presence of a granular esterification catalyst, 4. The method of claim 1, wherein the volume ratio of said portion to said output is about 0.5:1 to 5:1.

5. The method of claim 4, wherein said volume ratio is about 1:1 to 2:1.

6. The method of claim 1, wherein the weight ratio of terephthalic acid to methanol is about 1:3.

7. The method of claim 6, wherein the esterification takes place at a temperature of about 290° to 330°C.

8. A continuous method for the preparation of dimethyl terephthalate by the esterification of terephthalic acid with methanol in the gas phase at a temperature of about 290°–330°C, comprising:
   a. vaporizing solid terephthalic acid with a hot methanol vapor stream in a pre-reactor in a ratio of terephthalic acid to methanol of about 1:3 by weight;
   b. introducing the reaction product of the pre-reactor into a follow-up reactor having a solid bed granular esterification catalyst and producing a hot gaseous dimethyl terephthalate product stream having a given volume; and
   c. recirculating c. portion of said hot gaseous dimethyl terephthalate product stream to said pre-reactor of step (a) wherein the volume ratio of said portion to the remainder of said given volume is about 0.5:1 to 5:1 and heating said recirculated portion at a temperature of about 250° to 350°C.

9. The method of claim 8, wherein said portion is heated at a temperature of about 310° to 330°C.

* * * * *